United States Patent [19]

Ceriani et al.

[11] Patent Number: 5,766,571
[45] Date of Patent: Jun. 16, 1998

[54] METHOD OF TREATING HUMAN BREAST CANCER BY ADMINISTRATION OF RADIOLABELED ANTIBODY AND UNSATURATED FATTY ACIDS

[75] Inventors: Roberto L. Ceriani; Jerry A. Peterson, both of Lafayette, Calif.

[73] Assignee: Cancer Research Fund of Contra Costa, Walnut Creek, Calif.

[21] Appl. No.: 496,339

[22] Filed: Jun. 29, 1995

Related U.S. Application Data

[63] Continuation of Ser. No. 939,545, Aug. 31, 1992, abandoned, which is a continuation of Ser. No. 317,411, Mar. 1, 1989, abandoned.

[51] Int. Cl.$^6$ .................. A61K 39/395; A61K 51/00; A61K 31/00
[52] U.S. Cl. .................. 424/1.49; 424/138.1; 424/152.1; 424/155.1; 424/157.1; 424/178.1; 530/391.3; 530/387.7; 530/388.8; 530/388.85; 530/389.7
[58] Field of Search .................. 530/387.7, 388.85, 530/388.8, 389.7, 391.3; 424/135, 1.49, 138.1, 152.1, 155.1, 157.1, 178.1

[56] References Cited

FOREIGN PATENT DOCUMENTS 0256714   2/1988   European Pat. Off. .

OTHER PUBLICATIONS

Peterson, J.A., et al., "Biochemical and Histological Characterization of Antigens Preferentially Expressed on the Surface and Cytoplasm of Breast Carcinoma Cells Identified by Monoclonal Antibodies Against the Human Milk Fat Globule", Hybridoma 9:221–235 (1990).

Kramer, E. L. et al. "Radioimmunolocalization of Metastatic Breast Carcinoma Using Indium–111–Methyl Benzyl DTPA BrE–3 Monoclonal Antibody: Phase 1 Study" Radioimmunolocalization of Breast Cancer 34:1067–1074 (1993).

Mooi, W.J., et al., "Accessibility of antigenic sites recognized by AUA1, HMFG1 and HMFG2 mononclonal antibodies: its influence on antibody binding of live cells", The Int. J. of Biological Markers 2:57–63 (1987).

Bamias, A. et al "Intravesical Administration of Indium–111–Labelled HMFG2 Monoclonal Antibody in Superficial Bladder Carcinomas" Int. J. Cancer 54:899–903 (1993).

Epenetos, A.A. et al "Antibody–Guided Irradiation of Advanced Ovarian Cancer With Intraperitoneally Administered Radiolabeled Monoclonal Antibodies" J. of Cl. Oncology 5:1890–1899 (1987).

Kalofonos, H.P. et al "Antibody–Guided Diagnosis and Therapy of Malignant Lesions" Int. J. Cancer; Suppl 2:74–80 (1988).

Kosmas, H.P. et al "Radiolabelled Monoclonal Antibodies in Tumor Diagnosis and Therapy" Develop. biol. Standard 71:93–102 (1990).

Athanassiou, A. et al "Immunoscintigraphy with $^{131}$I–Labelled HMFG$_2$ and HMFG$_1$ F(ab')$_2$ In the Pre–Operative Detection of Clinical and Subclinical Lymph Node Metastases in Breast Cancer Patients" Int. J. Cancer, Suppl 3:89–95 (1988).

Pectasides, D. et al "Immunoscintigraphy with $^{131}$I–Labelled HMFG$_2$ and HMFG$_1$ F(ab')$_2$ Versus Abdominal CT Scan in the Detection of Residual Disease in Ovarian Cancer Patients" Int. J. Cancer, Suppl 3:83–88 (1988).

Pervez, S. et al "Localization of Monoclonal Antivbody AUA1 and Its F(ab')$_2$ Fragments in Human Tumor Xenografts: An Autoradiographic and Immunohistochemical Study" Int. J. Cancer Suppl 3:23–29 (1988).

Shepherd, J. et al "Tumour–associated monoclonal antibodies for the diagnosis and assessment of ovarian cancer" Br. J. of Ob/Gyn 94:160–167 (1987).

Dhokia, B. et al "A new Immunoassay using monoclonal antibodies HMFG1 and HMFG2 together with an existing marker CA125 for the serological detection and managment of epithelial ovarian cancer" Br. J. Cancer 54:891–895 (1986).

Dhokia, B. et al "A low pH enzyme linked immunoassay using two monoclonal antibodies for the serological detection and monitoring of breast cancer" Br. J. Cancer 54:885–889 (1986).

(List continued on next page.)

Primary Examiner—Lila Feisee
Assistant Examiner—Nancy A. Johnson
Attorney, Agent, or Firm—Viviana Amzel; Pretty, Schroeder & Poplawski

[57] ABSTRACT

An improved in vivo method of inhibiting or retarding the growth of malignant tumor cells in a subject comprises administering the subject antitumor therapy, the improvement comprising administering to the subject at least one product comprising an agent selected from the group consisting of polyunsaturated fatty acids, prostaglandins, prostacyclins, thromboxanes, leukotrienes, malonealdehyde, triene epoxides, analogs thereof, salts thereof and mixtures thereof, the antitumor therapy and the product being administered in amounts and for a period of time effective to attain the desired effect. An in vivo method of inhibiting or retarding the growth of malignant tumor cells comprises administering to a subject in need of such treatment at least one anti-cell antigen specific radiolabeled antibody and at least one product comprising an agent such as polyunsaturated fatty acids, prostaglandins, prostacyclins, thromboxanes, leukotrienes, malonealdehyde, triene epoxides, salts thereof and mixtures thereof, the antibody and the product being administered in amount and for a period of time effective to attain the desired effect. A kit for use in antitumor therapy comprises in separate containers an antitumor agent such as a chemotherapeutic agent, an anti-tumor hormonal agent, an anti-target cell antibody, external and an internal irradiation agents, or biological response modifiers, and an agent such as polyunsaturated fatty acids, prostaglandins, prostacyclins, thromboxanes, leukotrienes, malonealdehyde, triene epoxides, salts thereof or mixtures thereof.

20 Claims, 4 Drawing Sheets

OTHER PUBLICATIONS

Epenetos, A.A., et al, "Targeting of Iodine–123–Labelled Tumour–Associated Monoclonal Antibodies to Ovarian, Breast, and Gastrointestinal Tumours", The Lacet, 6 Nov. 1982: 999–1004.

"Effect of Fish Oil on Prostaglandin E and Tumor Lipid in a Human Mammary Carcinoma", Ceriani, R.L., Peterson, J.A., John Muir Cancer and Aging Research Institute, Draft #8: 1–29 (Aug. 5, 1991).

Blank, E.W., et al., "Fish Oil Enhancement of 131–Conjugated Anti–Human Milk Fat Globule Monoclonal Antibody Experimental Radioimmunotherapy of Breast Cancer", J. Steroid Biochem., vol. 34, Nos. 1–6, pp. 149–153 (1989).

Ceriani, R.L., et al, "Immunotherapeutic Preclinical Evaluation of Anti–Human Milk Fat Globule MoAbs MC5 & BrE–1", Antibody, Immunoconjugates, & Radiopharmaceuticals vol. 3, No 3: 181–198 (1990).

Ceriani, R.L., et al, "Development and Characterization of Breast Carcinoma Cell Lines as in Vitro and in Vivo Models for Breast Cancer Diagnosis and Therapy", Program Project Grant: Breast Cancer Therapy 1–P01–CA42767, Appendix 6:1–29, (May 13, 1991).

Ceriani, R.L., et al, "Biodistribution and Radioimmunotherapy in Eight Antibodies against the Breast Epithelial Mucin with Diverse Characteristics Labeled with $^{131}$In, $^{111}$In and $^{90}$Y", Program Project Grant: Breast Cancer Therapy 1–P01–CA42767, Appendix 7:1–41 (1991).

DeNardo, S.J., et al, "Radioimmunotherapy with I–131 Chimeric L–6 in Advanced Breast Cancer", In: Breast Epithelial Antigens: Molecular Biology Clinic Application, Ceriani, R.L., e.d., Plenum Publishing, pp. 227–232 (1991).

Ceriani, R.L., & Blank, E.W., "Experimental Therapy of Human Breast Tumors with $^{131}$I–Labeled Monoclonal Antibodies Prepared against the Human Milk Fat Globule", Cancer Research 48;4664–4672 (1988).

Peterson, J.A., et al, "Biochemical and Histological Characterization of Antigens Preferentially Expressed on the Surface and Cytoplasm of Breast Carcinoma Cells Identified by Monoclonal Anti–bodies Against the Human Milk Fat Globule", Hybridoma 9(3):221–235 (1990).

Ceriani, R.L., et al, "Experimental Immunotherapy of Human Breast Carcinomas Implanted in Nude Mice with a Mixture of Monoclonal Antibodies Against Human Milk Fat Blobule Components", Cancer Research 47:532–540 (Jan. 15, 1987).

Ceriani, R.L., et al., "Characterization of Cell Surface Antigens of Human Mammary Epithelial Cells with Monoclonal Antibodies Prepared Against Human Milk Fat Globule", Somatic Cell Genetics 9(4):415–427 (1983).

"Proceedings of the AOCS Short Course on Polyunsaturated Fatty Acids and Eicosanoids", Lands, W.E.M., Ed., American Oil Chemists' Society, Champaign, IL, May 14–17, 1987 in Biloxi, MS.

CRC Handbook of Eicosanoids: Prostaglandins and Releated Lipids, vol. 1, Chamical and Biochemical Aspects, Part A, Willis, A.L., Eds., CRC Press Inc., pp. 3–46 Boca Raton FL (1987).

Karmall et al., J. Nat. Cancer Inst. 73:457 (1984).

Begin et al., J. Nat. Cancer Inst. 9:188 (1988).

Reitz et al in Proceedings of the AOCS Short Course on Polyunsaturated Fatty Acids and Eicosanoids, Ed. Lands, W.E.M, American Oil Chemists'Society. Champaign, Illinois; pp. 529–533 (1987).

Wetherall et al, "Antiproliferative Effect of Vitamin A on Xenotransplanted CaMa–15 Cells", Cancer Res., 44, 2393–2397 (1984).

Fraker et al, "Growth Inhibition by Retinol of a Human Breast Carcinoma Cell line in Vitry and in Athymic Mice", Cancer Res., 44, 5757–5763, (Dec. 1984).

Blank, E.W. et al., "A Novel Anti–breast Epithelial Mucin MAb (BrE–3), Characterization and Experimental Biodistribution and Immunotherapy", The Cancer Journal, vol. 5 No. 1 38–44 (1992).

De Nardo, S.J. et al., "Treatment of B Cell Malignants with $^{131}$ILYM–1 Monoclonal Antibodies", Int. J. Cancer. Suppl. 3.96–101 (1988).

Peterson, J.A. et al., "Molecular Analysis of Epitopic Heterogeneity of the Breast Mucin", In: Breast Epithelial Antigens., Ed. by Ceriani, R.L., Plenum Press, New York, pp. 55–68 (1991).

Ceriani, R.L. et al., "Breats Epithelial Antigen Levels and Breast Tumor Antigen Content", Breast Cancer Res. Treat 17, 55–58 (1990).

Ferreti, A. et al., "Effect of Fish Oil Supplementation on the Excretion of the Major Metabolite of Prostaglandin E in Healthy Male Subjects", Lipids, vol. 26, No. 7, 500–503 (1991).

Henderson, C. D. et al., "Influence of Omega–3 and Omega–6 Fatty Acid Sources on Prostaglandin Levels in Mice", Lipids, vol. 24, No. 6, 502–505 (1989).

Harris et al., Tibtech, 1993, 11:42.

Osband et al., Immunol. Today, 1990, 11:193.

Waldmann Science 252:1657 1991.

METHOD OF TREATING HUMAN BREAST CANCER BY ADMINISTRATION OF RADIOLABELED ANTIBODY AND UNSATURATED FATTY ACIDS

This application is a continuation of application Ser. No. 07/939,545 filed Aug. 31, 1992 now abandoned, which is a continuation of Ser. No. 07/317,411 filed Mar. 1, 1989, now abandoned.

TECHNICAL FIELD

This invention relates to a method for enhancing existing cancer therapies by additionally administering unsaturated fatty acids to a patient. More particularly, this invention relates to a method for enhancing existing breast cancer therapies such as surgery, chemo-, hormone- and radio-immunotherapy with radioactively labeled monoclonal antibodies by concomitantly administering to a patient specific types of polyunsaturated fatty acids. Of particular relevance to this invention are oils and fats comprising fish-type polyunsaturated fatty acids with high contents of omega-3 and/or omega-6 unsaturated bond contents. Still more particularly, this invention relates to a method for administering to humans fish oil-type products to enhance the effectiveness of other treatments of breast tumors, disseminated or not, with radioactively conjugated anti-breast antibodies such as monoclonal antibodies and other therapies.

BACKGROUND ART

Monoclonal antibodies have been raised with human milk fat globules as an immunizing agent (Taylor-Papadimitriou, et al., Int. J. Cancer 28:17 (1981); Ceriani, et al., Som. Cell Gen. 9:415 (1983)). These monoclonal antibodies have been shown in the past to bind to human breast tumors (Ceriani, et al., Cancer Res. 44:3033 (1984); Peterson, et al., Imperial Cancer Res. Fund, London, England Conference (1981)). Different breast tumor cells have also been used as the immunizing agent (Papsidero, et al., Cancer Res. 43:1741–1747 (1983)).

The above described, as well as other monoclonal antibodies, have been employed in immunotherapy studies. In these prior art studies, one or more monoclonal, antibodies were successfully administered, separately or in mixtures, to treat human breast tumors previously transplanted into immunosuppressed rodents (Capone, et al., J. Nat. Cancer Inst. 72:673 (1984); Ceriani, et al., Cancer Res. 47:532 (1987)).

Monoclonal antibodies raised against specific tumors, other than those described above, have also been proven to be effective for treating the target tumors carried by immunodeficient mice (Sharkey, et al., Cancer Res. 48:3270 (1988)).

Other anti-breast monoclonal antibodies labeled with radioactive elements were also successfully used in radio-immunotherapy against breast cancer cells which were additionally transplanted into an immunodeficient rodent (Ceriani, et al., Cancer Res. 48:4664 (1988)).

The radioactively labeled anti-breast monoclonal antibodies were shown to be far more effective in treating human breast tumors grafted in immunodeficient mice than were the respective unlabeled anti-breast monoclonal antibodies themselves (Ceriani, et al., Cancer Res. 48:4664 (1988)). It was thus demonstrated that the effect of anti-breast monoclonal antibodies on malignant cells was substantially increased by the addition of a radiolabel to the antibody molecule. This substantial increase in the activity of the antibodies was the result of the irradiation provided by the radioactive element conjugated to the monoclonal antibody. The radioactive element was delivered to the target site by the antibody which had the capability of specifically bonding to the breast tumor.

It has also been known for some time that the rate of growth of mouse carcinomas transplanted into syngeneic mice could be slowed by supplementing the diet with unsaturated fatty acids called MaxEPA obtained from fish oils (Karmali, et al., J. Nat. Cancer Inst. 73(2):457 (1984)). In addition, it has also been demonstrated that unsaturated fatty acids such as those which abound in fish oils, e.g., MaxEPA, can exert a tumoricidal action against breast tumor cells in tissue culture (Begin, et al., J. Nat. Cancer Inst. 77(5):1053 (1986); Begin et al., J. Nat. Cancer Inst. 80(3):188 (1988)).

In summary, the prior art shows that anti-milk fat globule monoclonal antibodies can retard the growth of human breast tumors and that this interfering action with the growth of human breast tumors can be magnified several fold by labeling the monoclonal antibodies with radioisotopic elements.

Chemotherapy (Stanton, et al., Cancer Res. 45:1862 (1985)), hormone therapy (Waxman, J., J. R., Soc. Med. 78:129 (1985)) and radiation therapy (Brady, L. W., et al., Cancer 55:2037 (1985)) are applied together with surgery as front line elements of treatments for cancers, specially for solid tumors, such as colon, breast, prostate, pancreas, brain, lung cancers. These therapeutic approaches are applied, each by itself, sequentially or simultaneously, depending on the stage of the cancer disease, the aggressiveness of the tumor or other conditions as is known in the art.

These known therapies, however, although demonstrably effective against breast tumors have not been shown to be capable of complete tumor erradication.

Thus, there is still a need for improved therapeutic methods which afford a higher degree of effectiveness for retarding and/or eradicating tumor cells without severe side effects.

DISCLOSURE OF THE INVENTION

This invention relates to an in vivo method of inhibiting the growth of malignant tumor cells, which comprises administering to a subject in need of such treatment an anti-tumor effective amount of at least one anti-cell antigen specific antibody; and administering to said subject at least one product comprising an agent selected from the group consisting of polyunsaturated fatty acids, prostaglandins, prostacyclins, thromboxanes, leukotrienes, malonealdehyde, triene epoxides, analogs thereof, pharmaceutical salts thereof and mixtures thereof, said antibody and said product being administered in amounts and for a period of time effective to attain said effect.

Also part of this invention is an article of manufacture or kit comprising in separate containers an anti-tumor agent selected from the group consisting of a chemotherapeutic agent, an anti-tumor hormonal agent, an anti-target cell antibody, external and internal irradiation, internal irradiation, hyperthermia and biological response modifiers; and a composition of matter comprising at least one agent selected from the group consisting of polyunsaturated fatty acids, prostaglandins, prostacyclins, thromboxanes, leukotrienes, malone-aldehyde, triene epoxides, analogs thereof, pharmaceutical salts thereof and mixtures thereof.

Biological response modifiers in the context of this application refers to molecules such as interferons, interleukins, tumor necrotic factor, etc. which are known in the art to affect lymphocytic cells such as T-cell lymphocytes and/or their activities.

Also part of this invention is an improved in vivo method inhibiting or retarding the growth of malignant tumor cells in a subject which comprises administering to the subject anti-tumor therapy, the improvement comprising administering to said subject at least one product comprising an agent selected from the group consisting of polyunsaturated fatty acids, prostaglandins, protacyclins, thromboxanes, leukotrienes, malonealdehyde, triene epoxides, analogs thereof, pharmaceutical salts thereof and mixtures thereof, said antibody and said product being administered in amounts and for a period of time effective to obtain said effect.

A more complete appreciation of the invention and many of the attendant advantages thereof will be readily perceived as the same becomes better understood by reference to the following detailed description when considered in connection with the accompanying figures.

Other objects, advantages and features of the present invention will become apparent to those skilled in the art from the following discussion.

BEST MODE OF CARRYING OUT THE INVENTION

This invention arose from a desire by the inventors to improve on prior art cancer therapies such as those involving surgery, chemotherapy and hormonal target-specific antibody and radiolabeled antibody therapies, among others.

This invention provides an improved in vivo method of inhibiting or retarding the growth of malignant tumor cells in a subject, comprising administering to the subject anti-tumor therapy, the improvement comprising administering to said subject at least one product comprising an agent selected from the group consisting of polyunsaturated fatty acids, prostaglandins, prostacyclins, thromboxanes, leukotrienes, malonealdehyde, triene epoxides, analoges thereof, pharmaceutical salts thereof and mixtures thereof, said anti-tumor therapy and said product being administered in amounts and for a period of time effective to attain said effect.

In accordance with the method of the invention the product can be administered to the subject prior to, in conjunction with or subsequent to various known anti-tumor therapies also intended for anihilation, the inhibition or retardation of the growth of the malignant tumor cells.

These therapies are known in the art and an artisan would know which specific therapy is most appropriate for particular types of tumor cells. By means of example the present method may be practiced by administering the product in combination with chemotherapy and/or radioimmunotherapy.

Chemotherapy Radiotherapy may be administered either orally, systemically or by other routes, either using a single agent or a multiplicity of agents thereof. Typically, chemotherapeutic agents include alkylating agents, antimetabolites, anthracycline and other types of antibiotics, among others, either alone or in mixtures thereof (Seiger, T., et al, in Cancer of the Breast, third Ed., Donagan W., et al, p. 475, Saunders, W. G., Eds. (1988), the entire content of which is incorporated herein by reference).

Hormonal therapy may be administered either as a medicine or by means of the ablation of hormone-secreting organs in the subject. Typically, hormonal drugs which may be utilized encompass estrogen analogs such as tamoxifen, aromatase inhibitors, progesterone analogs and other types of competing hormone analogs known in the art. The surgical ablation includes procedures such as ovariectomy, adrenalectomy and hypophysectomy, either alone or as a combination thereof (Kardinal, C., in Cancer of the Breast, Donagan W. et al, p. 501, Saunders W. G., eds, third Edition (1988), the entire contents of which is incorporated herein by reference).

Radiotherapy may be external, which is the most commonly used, or internal. External radiotherapy is typically applied locally in an area which was previously subject to surgery or to the axilla. On occasion, radiotherapy may be used to treat distant metastases as well. At this point in time internal radiotherapy is not used frequently. However, when utilized, it is delivered by radioactively laden needles which are inserted on a particular lesion which is to be treated (Wilson et al. in Cancer of the Breast, Donagan W. et al. p. 462, Saunders W. G., Ed. third Edition (1988), the entire content of which is incorporated herein by reference).

The present products may also be administered pre- or post-tumor surgery either for the treatment of the primary tumor or occasionally for the treatment of metastatic lesions of cancer, e.g., breast cancer, among others (Carter, S., "Hormone and Chemotherapy: Fundamental Clinical Concepts", in Breast Cancer: Diagnosis and Treatment, Ariel, I. M. and Cleary, J. B., eds., McGraw-Hill, N. Y., pp. 358–378 (1987)).

Another type of cancer tumor therapy is hyperthermia, which may be administered either localized or systemically. This treatment has often been utilized in the past for the treatment of breast cancer (Song, C., in A Categorical Course in Radiation Therapy: Hyperthermia, Steeves, R. A. et al, Radiological Society of North America, p. 17 (1987), the entire content of which is incorporated herein by reference).

Radioimmunotherapy is most effectively conducted by binding radioactive atoms to monoclonal antibodies having affinities and/or specificities for a particular type of target cell. Monoclonal antibodies are typically secreted by hybridomas which may be prepared in accordance with the technology developed by Kohler and Milstein (Kohler, G. and Milstein, C., Nature (London) 256:494–497 (1975); Herzenberg and Milstein, Handbook of Experimental Immunology, pp. 25.1–25.7, Ed. Weir (Blackwell Scientific, London) (1979), the entire contents of which are incorporated herein by reference).

The radiolabeled atoms which may be utilized in the above technology are also known in the art as is the technology involved in the binding of the radiolabeled atoms to the antibody molecules (Hunter, et al., Nature 194:495 (1962); Hnatowich, et al., Science 220:613 (1983)).

Typically, the antibodies are labeled with a radioactive atom such as $^{131}$I, $^{90}$Y, $^{212}$Bi, $^{186}$Re, $^{221}$At, $^{99m}$Tc and mixtures thereof. However, other radioactive atoms may also be utilized as is known in the art.

The antibody utilized in the anti-tumor therapy may be a polyclonal antibody or a monoclonal antibody. However, it has to have affinity for a specified type of tumor cell so that it can be directed to bind to a target tissue for which it has affinity.

Other forms of cancer tumor therapy may also be utilized in combination with the administration of the present product in accordance with the method of this invention.

The amounts and modes of administration of the other anti-tumor therapies are only peripherally part of this invention and information thereof can be found in the public domain.

In a particularly desirable embodiment of the invention the agent utilized in the method is a fatty acid which is selected from the group consisting of essential fatty acids, analogs thereof, pharmaceutically acceptable salts thereof, mixtures thereof and mixtures thereof with the other agents.

Typically, the fatty acids will be polyunsaturated and will have ($C_{12}$–$C_{30}$) atoms. Of particular importance are eicosanoids or fatty acids which ultimately produce arachidonic acids which is involved in the synthesis of prostaglandins (CRC Handbook of Eicosanoids: Prostaglandins and Related Lipids, Vol. I: Chemical and Biochemical Aspects, Part A, Willis A. L., pp. 3–46, CRC Press, Inc. Boca Raton, Florida (1987), the entire content of which is incorporated herein by reference).

Also particularly preferred for the practice of this invention are polyunsaturated fatty acids of the fish oil type such as, e.g., MaxEPA, linoleic, C18:2n-6 (1.6%), alpha-linoleic, C18:3n-3 (2.8%), 18:4n-3 (2.6%), arachnidonic, C20:4n-6 (2.7%), eicosopentanoic, C20:5n-3 (17.6%), C22:5n-3 (2.9%) and docasahexaenoic, C22:6n-3 (12.2%), among others, derivatives thereof, analogs thereof, pharmaceutically aceptable salts, thereof, mixtures thereof and mixtures thereof with the other agents.

The CRC Handbook of Eicosanoids publication, supra, provides extensive information on the types of essential fatty acids which are encompassed by this invention and the practitioner is referred to its disclosure in order to select particular fatty acids or products containing them which are suitable for the practice of this invention under different conditions.

By means of example, the products utilized herein may be polyunsaturated fatty acids, and among these preferred are essential fatty acids, and among these preferred are derived essential fatty acids (e.g., $C_{20}$, fatty acids), and more preferred are eicosanoids and omega-3 and omega-6 polyunsaturated fatty acids, cyclo-oxigenase products, 5- 12- or 15-lipoxigenase products, monooxigenase products, prostaglandins, prostacyclins, thromboxanes, leukotriens, malonedialdehyde, $C_{17}$-hydroxy fatty acids, 12-HpETE, analogs thereof, 12-HETE, analogs thereof and triene epoxides, derivative thereof, analogs thereof, pharmaceutical salts thereof, mixtures thereof and mixtures thereof with the remaining agents, among others.

One of the most preferred products utilized for the practice of this invention are fish oils. Fish oils contain a complex mixture of fatty acid moieties, mostly straight chain with even numbers of carbon atoms. These moieties, mainly present as their glycerides, are either saturated or mono- or polyunsaturated. Whereas vegetable oils and fats from terrestrial animals are composed mainly of fatty acids containing a maximum of 18 carbons and two or three double bonds, fish and marine mammal oils are composed of substantial amounts of fatty acid moieties containing 20 or 22 carbons and four, five or six double bonds (Stansby, "Fish Oils" Avi Publishing Company, Inc. (1967)).

Among the fatty acid moieties unique to fish oils are the following n-3 and n-6 compounds: 18:4, 20:4, 20:5, 22:4, 22:5, 22:6. As generally used, n-3 or omega-3 or n-6 or omega-6 means that the first double bond begins at the third carbon counting from the methyl end of the chain. In the number:number designation, the first number indicates the chain length and the second number indicates how many double bonds are present. For example, 18:4 indicates a straight chain comprised of 18 carbon atoms containing 4 methylene-interrupted double bonds.

The polyunsaturated components of fish and marine mammal oils are of particular interest because they differ significantly from those found in vegetable oils or fats from terrestrial animals. Highly unsaturated fatty acids, such as those contained in fish oils have been known to be important dietary factors beneficial in reducing the development of atherosclerotic lesions (Dyerberg et al, "Nutritional Evaluation of Long-chain Fatty Acids in Fish Oil", pp. 245–261, Academic Press, London (1982)). Polyunsaturated fatty acids present in fish oils can also be utilized in a more concentrated form (U.S. Pat. No. 4,675,132).

Also suitable for use with the method of the invention are derivatives and analogs of the above products. The analogs of the invention are similar to the corresponding agents such as fatty acids except for the presence of an organic substituent at the C3, C5, C7 or C9 position, and, in some embodiments, a second organic substituent bonded to the antepenultimate carbon of the chain.

Any organic substituent of the derivative or analog should be small enough to permit the formation of the first chemical intermediate involved in the fatty acid beta- or omega-oxidation process. Too large a substituent can alter the uptake and analogy behavior of the analog to an undesirably great extent. It is preferred that the substituent be an alkyl or heteroalkyl (alkyl containing one or more atoms other than hydrogen or carbon) group containing one to three carbon atoms, inclusive, an aryl or heteroaryl (aryl containing one or more atoms other than hydrogen or carbon) group having one or two aromatic rings each having six or fewer carbon atoms, or an aralkyl or heteroaralkyl group having one or two aromatic rings each having six or fewer carbon atoms and an alkyl group having one to three carbon atoms, inclusive. Also preferred are halogen substituents.

The chemical nature, as well as the size, of any substituent can affect the properties of the derivative or analog. Generally, the derivative or analog should have a substituent which does not render it excessively polar, e.g., an unsubstituted alkyl group or a polarizing group, e.g., an ether, or alcohol. Generally, a chain length of 7–30 carbon atoms, inclusive, is suitable for the polyunsaturated fatty acids.

The derivatives of the agents may contain a larger or smaller number of C-atoms and/or substitutents of any kind as long as they do not interfere with the noted activity of the agents.

In another particularly preferred embodiment the method of the invention is practiced where the polyunsaturated fatty acids are selected from the group consisting of derived essential fatty acids, omega-3 and omega-6 polyunsaturated fatty acids and combinations thereof, analogs thereof, pharmaceutically-acceptable salts thereof and mixtures thereof, and mixtures thereof with the other agents.

In a still more preferred embodiment of the invention wherein the fatty acids of ($C_6$–$C_{50}$) fatty acids comprising three or more unsaturated bonds, analoges thereof, pharmaceutically-acceptable salts thereof, mixtures thereof and mixtures thereof with the remaining agents.

Typically, the amount of product administered to a subject is about 0.3 g to 6.0 g per Kg of body weight of the subject and it is administered every about 1 to 60 hours, and more preferably about 0.9 g to 2.5 g per Kg every about 6 to 24 hours or more. Typically, the product of the invention may be administered by an oral, systemic, parenteral or rectal route, or by a combinations thereof. When administered orally the product may be admixed with the subject's food in an amount of about 1 to 50 wt % thereof, more preferably about 2 to 30 wt % thereof, and most preferably about 5 to 20 wt % thereof.

As already indicated above the different anti-tumor therapies may be administered the subject such as surgery, chemotherapy, target-specific antibody therapy which may be unlabeled or radiolabeled, and hormonal therapy, among others, and combinations thereof in combination with the administration of the product as disclosed herein.

The administration of the present product may be conducted prior to, during or subsequent to the other anti-cancer therapies. By means of example, surgery may be conducted first and subsequent to it a subject may be administered chemotherapy and/or a diet of the present products. Equally possible is the administration of hormonal therapy with or without chemotherapy and subsequently or simultaneously the present products may be administered to the subject. Other combinations are also possible and may be utilized at the discretion of the practitioner.

This invention also provides an in vivo method for inhibiting or retarding the growth of malignant tumor cells, which comprises administering to a subject in need of such treatment at least one anti-cell antigen specific antibody; and administering to said subject at least one product comprising an agent selected from the group consisting of polyunsaturated fatty acids, prostaglandins, prostacyclins, thromboxanes, leukotrienes, malonealdehyde, triene epoxides, analoges thereof, pharmaceutical salts thereof and mixtures thereof, said antibody and said product being administered in amounts and for a period of time effective to attain said effect.

In general this method may be practiced following the same guidelines as the method described above.

The antibodies may be polyclonal or monoclonal. Preferred are monoclonal antibodies, and still more preferred are radioactively-labeled monoclonal antibodies. The antibodies may be labeled with ax radioactive atom such as $^{131}$I, $^{90}$Y, $^{212}$Bi, $^{186}$Re, $^{99m}$Tc, $^{221}$At or admixtures thereof. However, other radioactive atoms may also be utilized.

The products utilized in conjunction with other anti-tumor therapies are similar to those described above as are the amounts and routes of administration thereof.

Also part of this invention is a kit or article of manufacture comprising in separate containers an anti-tumor agent selected from the group consisting of chemotherapeutic agent, an anti-tumor hormonal agent, an anti-target cell antibody, external radiotherapy, internal radiotherapy, hyperthermia, and biological response modifiers; and a composition of matter comprising at least one agent selected from the group consisting of polyunsaturated fatty acids, prostaglandins, prostacyclins, thromboxanes, leukotrienes, malone-aldehyde, triene epoxides, analoges thereof, pharmaceutical salts thereof and mixtures thereof.

In a particularly useful embodiment of the invention the kit further comprises at least one syringe and needle and it is intended for self-administration.

The other anti-tumor agents are selected from the group described above and may typically be a chemotherapeutic agent, and anti-tumor hormonal agent, surgery, hormonal and/or hyperthermic therapy and the like. These are known in the art and need not be described further herein.

In a preferred embodiment of the invention the antibody is labelled with a radioactive atom selected from the group consisting of $^{131}$I, $^{90}$Y, $^{212}$Bi, $^{186}$Re, $^{221}$At, $^{99m}$Tc and mixtures thereof.

In still another preferred embodiment of the invention the fatty acid is selected from the group consisting of essential fatty acids, derivatives thereof and synthetic fatty acids comprising fish oil-type fatty acids, cyclooxigenase products, 5-, 12- and 15- cyclooxygenase products, monooxigenase products, $C_{17}$12-HpETE, $C_{17}$12-HETE, analogs thereof, pharmaceutically-acceptable salts thereof and mixtures thereof.

A still more preferred embodiment of the invention is that wherein the fatty acids are selected from the group consisting of derived essential fatty acids, omega-3 and omega-6 polyunsaturated fatty acids and combination thereof, analogs thereof, pharmaceutically-acceptable salts thereof and mixtures thereof.

In still a more preferred embodiment of the invention the fatty acids are ($C_6$–$C_{30}$) fatty acids, and still more preferably ($C_{12}$–$C_{25}$) fatty acids, comprising three or more unsaturated bonds, analogs thereof, pharmaceutically-acceptable salts thereof.

A most preferred embodiment of the invention is that where the antibody has specificity for a specific type of cell such as those associated with a particularly specialized tissue. Examples are antibodies having specificities for epithelial cells and/or their tumors, colonic cells and/or their tumors, pancreatic cells and/or their tumors, breast cells and/or their tumors, lung cells and/or their tumors, prostate cells and/or their tumors and the like. A particularly preferred group encompasses antibodies having high affinities for particular human target tissue cells, and optionally also specificity thereto, e.g., human breast cells. In this case, the article is intended for inhibiting or retarding the growth of malignant human breast tumor cells.

In a particularly useful embodiment of the invention the antibody is provided in a closed sterile container and the product is provided in a light-impermeable container in the form of a powder, capsules, dragees(J, tablets, a liquid solution or suspension or suppository, among others.

Having now generally described this invention, the same will be better understood by reference to certain specific examples, which are included herein for purposes of illustration only and are not intended to be limiting of the invention or any embodiment thereof, unless so specified.

EXAMPLES

Example 1
Transplantation of Human Mammary Tumors Into Mice.

Female BALB/c nu/nu mice were injected subcutaneously with 50 mm$^3$ of a suspension of finely minced human mammary adenocarcinoma MX-1 in Dulbecco's minimal medium (DME) (Gibco Grand Island, N.Y.), proximal to the right #4 mammary gland using a 16 gauge needle under sterile conditions. The mice were obtained from Life Sciences, St. Petersburg, Fla., and were housed in sterilized plastic cages, with sterilized filter tops and bedding in a temperature-controlled room at 25.5°–27.8° C. on a 12:12 hour light:dark cycle. The diet and pH 2.5-acidified distilled water were made available to the animals ad libitum. The mice were maintained on a standard laboratory diet which contains 11 wt% fat (Purina Mouse Chow #5015).

Example 2

Effect of Various Diets on Transplanted Human Mammary Tumors:

At 5 days after implantation the mean tumor volume being approximately 90 mm$^3$, 12 mice were separated into three groups and each mouse was given a designated, semi-purified, isocaloric experimental diet containing 11 wt. % fat.

The fat component consisted of lard (Group I), corn oil (CO) (Group II), or MaxEPA which is a fish-type oil low in monosaturates and vitamin D supplemented with vitamin E (Group III). The fat component was added to a fat-free dry mixture.

The fat-free dry mixture contained by weight the following components.

54.5% glucose;
23.7% vitamin-free casein;
3.4% salt mixture (AIN #76);
2.2% vitamin mixture (vitamin diet fortification mix, ICN, Cleveland, Ohio);
0.3% methionine;
4.9% cellulose; and
0.01% butylated hydroxytoluene.

The fat-containing diets were made by adding 11 wt. % of each fat or oil described above to the dry mixture. The fat component included either lard (Armour Food Co., Omaha, Nebr.), CO (Willsey Foods, City of Industry, Calif.) or MaxEPA (R. P. Scherer Corp., Clearwater, Fla.).

Fresh diets were made twice a week, dried and frozen. New pellets were fed daily to standardize the intake of the fatty acids and to prevent their possible peroxidation if left in the cages for longer periods of time.

The fatty acid analysis of each fat or oil, determined by standard gas-liquid chromatographic methods, is given in Table 1 below.

TABLE 1

Predominant fatty acid composition of dietary fats

| | Percent of total fatty acids | | |
|---|---|---|---|
| Fatty Acids | Lard | Corn oil | MaxEPA |
| 16:0 | 24.7 | 11.7 | 10.3 |
| 16:1 | 2.9 | 0.1 | 8.8 |
| 18:0 | 14.6 | 1.9 | 3.8 |
| 18:1 | 45.0 | 25.2 | 15.5 |
| 18:2, n-6 | 8.0 | 59.7 | 1.2 |
| 18:3, n-3 | 1.4 | 1.4 | 2.8 |
| 18:4, n-3 | 0.1 | — | 2.6 |
| 20:4, n-6 | 0.2 | — | 2.7 |
| 20:5, n-3 | — | — | 17.6 |
| 22:5, n-3 | 0.1 | — | 2.9 |
| 22:6, n-3 | — | — | 12.2 |
| Total | 97 | 100 | 80.4 |

Fatty acids were identified and quantitated by standard gas-liquid-chromatography and are expressed as the number of carbons: number of double bonds, position of the first carbon from the end-methyl group of the fatty acid.

Figure 2:
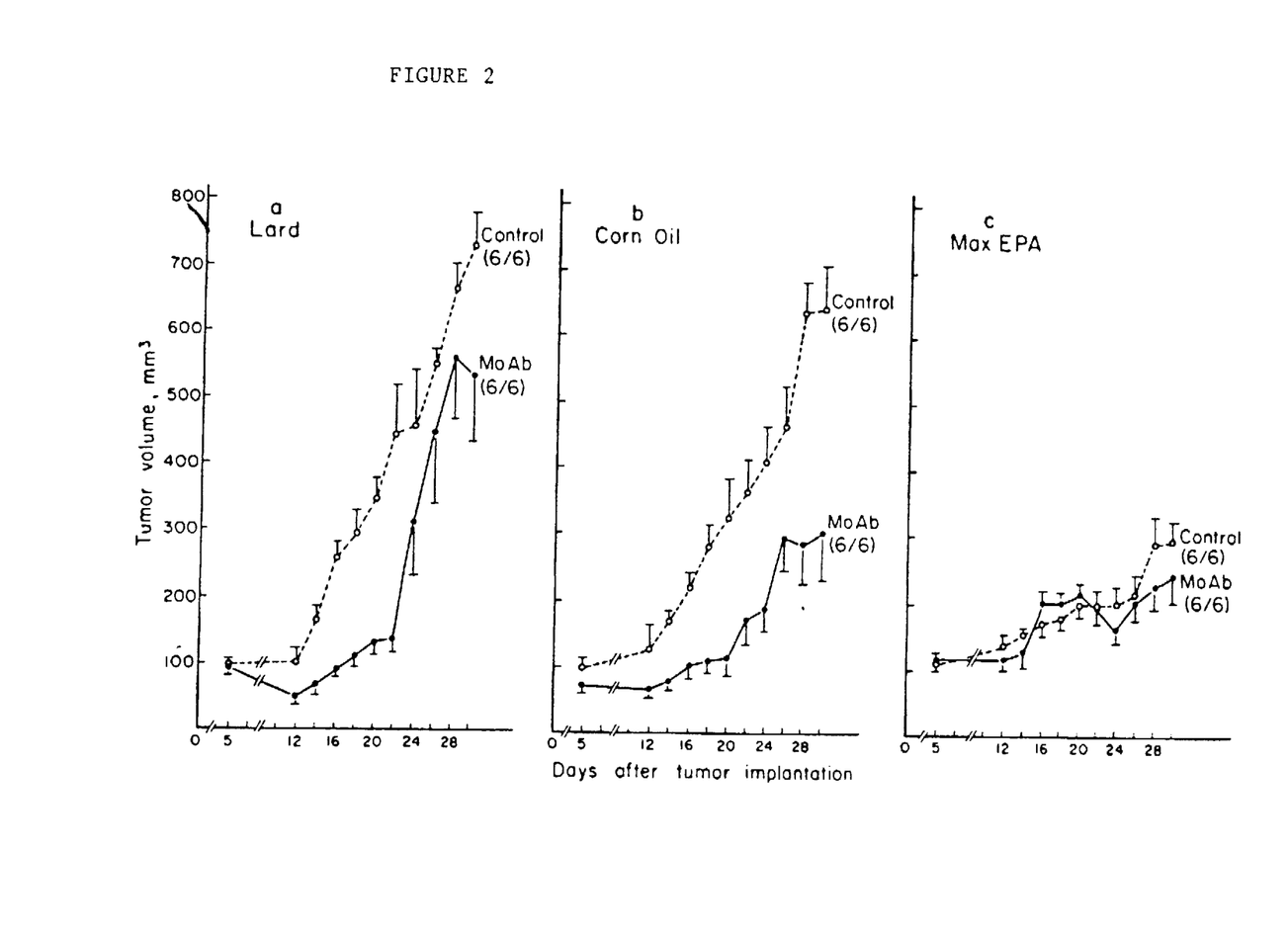
FIG. 2A shows the effect of monoclonal antibody and dietary fat consisting of MaxEPA on the growth of the MX-1 human mammary tumor in BALB/c nude mice. Each point represents the average of 6 animals. The standard deviation is shown by a bar.
FIG. 2B shows the effect of monoclonal antibody and dietary fat consisting of corn oil on the growth of the MX-1 human mammary tumor in BALB/c nude mice. Each point represents the average of six animals, and the standard deviation is shown by a bar.
FIG. 2C shows the effect of monoclonal antibody and dietary fat consisting of lard on the growth of the MX-1 human mammary tumor in BALB/c nude mice. Each point represents the average of six animals, and the standard deviation is shown by a bar.

A significantly larger reduction in the growth of human mammary adenocarcinoma MX-1 was achieved when female BALB/c nu/nu mice were fed an 11 wt % fat isocaloric diet containing polyunsaturated fatty acids (PUFA) in the form of a blend of purified fish oils (MaxEPA) when compared with the polyunsaturated fatty acid (PUFA) diet containing corn oil (CO) or the mostly saturated fat diet containing lard. These data are shown in FIG. 2.

1.2 wt. % of the fatty acid constituents of MaxEPA is the n-6 essential fatty acid (EFA) linoleate (C18:2), and 17.6 wt. % and 23.2 wt. % are the n-3 and n-6 PUFAs eicosapentaenoate (EPA; C20:5) and docosahexaenoate (DHA; C22:6) respectively.

On the other hand, 59.7 wt. % of fatty acid constituents of CO ire present as linoleate. Lard contains mainly saturated fatty acids (SFAs). It has 8.5 wt. % linoleate and small amounts of others as shown in Table 1 above.

MaxEPA retarded the growth of the neoplasms significantly more from days 20 and 22 respectively until the termination of the experiment when compared to the effects seen with the effect of lard or CO diets. Thus, feeding MaxEPA to the animals resulted in only a 335% increase in tumor volume during the experimental period whereas CO feeding increased tumor volume by 609% and lard feeding increased tumor volume by 838%. These data are shown in FIG. 2.

Figure 1:
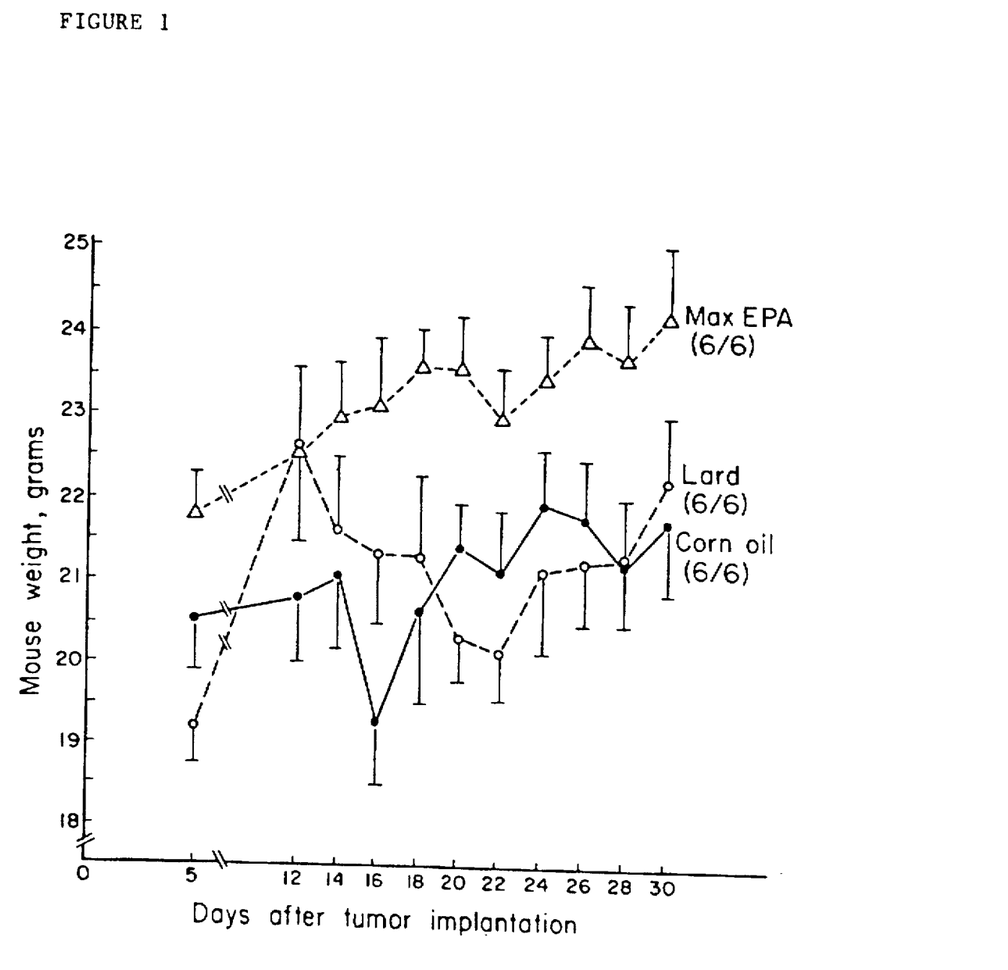
FIG. 1 shows the effect of a sole dietary fat source consisting of either MaxEPA, corn oil or lard on bodyweight of BALB/c nude mice bearing MX-1, a transplantable human mammary tumor. Each point represents the average of 6 animals. The spread in values is shown by a bar and standard error.

Moreover, the observed tumor growth inhibition produced by MaxEPA was not due to an overall growth retardation of the animals. On the contrary, feeding MaxEPA resulted in a significant increase in mouse weight as compared to the weight of CO or lard fed animals. These data are shown in FIG. 1.

Furthermore, even though marine lipids contain significantly more cholesterol than vegetable oils such as CO the total cholesterol and high density lipoprotein (HDL)-cholesterol and triglyceride (TG) concentrations in sera of the MaxEPA-fed mice were approximately one-half of those found in the CO fed mice. These data are shown in Table 2 below.

TABLE 2

Values for cholesterol, high density liprotein and triglyceride in sera of nude mice grafted with MX-1 tumor at end of experiment.

in Serum

| Dietary Fat (11 wt %) | Total Cholesterol (mg/dl) | HDL Cholesterol | Cholesterol: HDL Ratio | TGL (mg/dl) |
|---|---|---|---|---|
| Lard | 89 | 85 | 1.1 | 125 |
| Corn Oil (CO | 104 | 91 | 1.1 | 122 |
| MaxEPA | 58 | 55 | 1.1 | 80 |

The total cholesterol, high density lipoprotein (HDL), cholesterol and triglyceride (TGL) content in serum was quantitatively measured after a 14 hour fast in a DuPont ACA clinical analyzer by standard procedures.

The same phenomenon was observed between the MaxEPA and lard-fed mice. However, no differences were found between the CO or lard fed groups and the phenomenon was thus assumed to be unrelated to the saturated and unsaturated nature of the fat in the diet.

In summary, the growth of experimental human breast tumors fed the polyunsaturated fish oil mixtures called Max-EPA was inhibited when compared to the growth obtained under isocaloric diets containing CO or lard as the sole fatty acid source.

Example 3
Effect of Combined Therapy of Fatty Acid Diets and Unconjugated Monoclonal Antibodies.

Five days after being placed on the experimental diets and 10 days after tumor grafting, 6 mice from each of the three groups described above were injected a 0.8 ml sample containing 2.4 mg protein of a mixture of equal protein amounts of monoclonal antibodies (MoAbs) Mc1, Mc3, Mc5 and Mc8 able to bind to human mammary epithelial antigens. These monoclonal antibodies were obtained as described in Ceriani, R. L. "Experimental immunotherapy of human breast carcinomas implanted in nude mice with a mixture of monoclonal antibodies against human milk fat globule components", Cancer Res. 47:532–540 (1987).

Nude mice (nu/nu) with a BALB/c background were purchases (Life Sciences, Inc., St. Petersburg Fla.). Female nu/nu mice were grafted with transplantable human tumors at 7 to 8 weeks of age (body weight, 19 to 24 g). They were placed in sterile cages with sterile bedding, one per cage, provided mouse chow (5015 Purina) and acidified (pH 2.5) water an libitum. Grafts where sterilely implanted through a flank incision midway between front and hind legs. The 1-mm-diameter graft was then gently pushed above the hip with fine forceps. The wound was closed with metal clips.

Transplantable, estrogen receptor-negative human tumors used were an MX-1 human breast carcinoma, a CX-1 human colon carcinoma derived from the HT-29 colon carcinoma cell line, and an LX-1 carcinoma derived from a metastatic human lung carcinoma. (inorie et al., "Antitumor Efficacy of Seventeen Anticancer Drugs in Human Breast Cancer Xenograft (MX-1) Transplanted in Nude Mice", Cancer Chemother. Pharmacol. 10:182–186 (1983)). These tumors were obtained from the EG&G Mason Research Institute and have been sterilely transplanted in our laboratory for years. An estrogen receptor-positive MCF-7 tumor was derived in our laboratory by injection of about $30 \times 10^6$ tissue culture cells into estrogen-primed female nu/nu mice. (Horwitz et al, "Steroid Receptor Analysis of Nine Human Breast Cancer Cell Lines", Cancer Res. 38:2434–2437 (1978); and Osborne et al., "Effect of Estrogen and Antiestrogens on Growth of Human Breast Cancer Cells in Athymic Nude Mice", Cancer Res. 45:584–590 (1985)). Each mouse was primed with a 178-estradiol 0.5 mg pellet (Innovative Research of America, Rockville, Md.) implanted in the interscapular area 2 days before tumor implantation and at 21-day intervals thereafter. For the experiments where monoclonal antibody treatment was administered to already established tumors, the tumors and their initial volumes were, respectively, 20 mm$^3$ and 80 mm$^3$ for MX-1, 70 mm$^3$ for MCF-7, and 75 mm$^3$ for CX-1, a non-breast tumor. Measurements of tumor growth performed in every case were with calipers by external measurement of the widest diameter, the narrowest diameter, and the height of the tumor. The formula for the volume of an ellipsoid was used to obtain volume values (volume=$\frac{4}{3}\pi ab^2$, where a is the largest radius and b is the average of 2 smaller radii).

The monoclonal antibodies used were those already described by Ceriani, R. L., et al., Somatic Cell Genetics 9(4):415–427 (1983) as follows. Briefly, the monoclonal antibodies were raised against HMFG membrane glycoproteins by injection into BALB/c mice and hybridization of their spleen cells with a mouse myeloma cell line (Sasalci et al., "Quantitation of Human Mammary Epithelial Antigens in Cells Cultured From Normal and Cancerous Breast Tissues", In Vitro (Rockville) 17:150–158 (1981); Ceriani et al., "Characterization of Cell Surface Antigens of Human Mammary Epithelial Cells with Monoclonal Antibodies Prepared Against Human Milk Fat Globule", Somatic Cell Genet. 9:415–427 (1983)). The thus obtained hybridomas were screened for positivity for HMFG and for negativity for cervical and colon carcinomas, normal human fibroblasts, and human lymphoid cells (Ceriani et al., (1983), supra). The hybridomas of monoclonal antibodies used to produce ascites were injected into 2, 6, 10, 14-tetramethylpentadecane-stimulated BALB/c mice with either hybridomas of Mc1, Mc3, Mc5, Mc8 monoclonal antibodies detected HMFG antigens with apparent molecular weights, respectively, of 400,000, 46,000, 400,000 and 46,000 (Ceriani et al., (1983), supra). Ascites was drawn and spun for 5 min. at 200×g. The supernatant was then spun at $1 \times 10^2 \times g$ in a refrigerated centrifuge for 10 min. and was finally filtered through a 0.2 µm Nalgene filter. The monoclonal antibodies were then tittered by end point dilution on 18-ng solid phase bound HMFG as already described by Ceriani et al. (Ceriani, R. L., "Solid Phase Identification and Molecular Weight Determinations of Cell Membrane Antigens with Monoclonal Antibodies", in Monoclonal Antibodies and Functional Cell Lines, Progress and Applications, Bechtol, K. B., McKern, T. J., and Kennett, R., eds., pp. 398–402, New York, Plenum Press, (1984). The ascites of X63A, the parent myeloma cell line, and normal mouse serum were used as controls. Normal mouse serum was obtained from BALB/c mice of either sex. Both control ascites and serum were processed and sterilized as monoclonal antibody ascites.

Each animal received a total of 10 intraperitoneal (i.p.) MoAb injections containing 2.4 mg protein at 48 hour intervals. The Mc1 and Mc5 MoAbs recognize 400,000 dalton components and the Mc3 and Mc8 MoAbs recognize 45,000 dalton components of the (HMFG) membrane protein (Ceriani, R. L. et al., "Characterization of cell surface antigens of human mammary epithelial cells with monoclonal antibodies prepared against human milk fat globule", Somat. Cell Genet. 9:415–427 (1983), the entire content of which is incorporated herein by reference).

The changes in animal weight and in tumor volume were determined before each MoAb injection and up to 30 days post implantation of the MX-1 tumor cells. These data are shown in FIG. 1.

Tumor volumes were obtained with a caliper as described in Ceriani et al (Ceriani, R. L., et al., "Experimeintal immunotherapy of human breast carcinomas implanted in nude mice with a mixture of monoclonal antibodies against human milk fat globule components", Cancer Res. 47:532–540 (1987)).

The calculation of the percent inhibition of growth (% IG) was performed using the formula $$\%IG=(1-Tn/To/Cn/Co)\times 100,$$

wherein

To and Tn are the mean tumor volumes at day 0 or day of initial unconjugated MoAb injection and day n respectively for the treated groups, and Co and Cn are the mean tumor volumes at day 0 or day of initial unconjugated MoAb injection and day n respectively for the control groups (Inoue, K. et al., "Antitumor efficacy of seventeen anticancer drugs in human breast cancer xenograft (MX-1) transplanted in nude mice", Cancer Chemother. Pharmacol. 10:182–186 (1983)).

Hybridoma cell lines, ascites collection, and pyrogen determination were performed as described in Ceriani et al. (Ceriani, R. L., et al., "Experimental immunotherapy of human breast carcinomas implanted in nude mice with a mixture of monoclonal antibodies against human milk fat globule components", Cancer Res. 47:532–540 (1987)).

Standard error of the mean value (SE) and its statistical significance were calculated using the student t test as described in Snedecor et al. (Snedecor, G. W., et al., "Statistical Methods", Ed. 6. Ames, IA: Iowa State University Press (1967)).

As the CO diet is an experimental equivalent of standard laboratory chow it was expected that the treatment of the animals with a monoclonal antibody mixture would effectively reduce the size of the tumors growing in the mice fed the CO-containing diet. Indeed, the monoclonal antibody treatment of CO-fed mice resulted in only a 365% increase in the control groups over the same time period of time counting from day one of injection or 30 days. These data are shown in FIG. 2.

Simultaneous treatment with anti-HMFG MoAbs show a definite therapeutic advantage in the CO fed group that is not shown in the other two diet supplemented groups. The present experimentation shows a synergistic role played by dietetic manipulation in the immune therapy of breast tumor (this is seen in the particular case where polyunsaturated fatty acid sources are fed the animals).

Example 4

Transplantation of Human Mammary Adenocarcinoma into Mice.

Mice were obtained from Life Sciences, Inc. (St. Petersburg, Fla.) and were maintained in a vivarium for the duration of the experiments. The mice were housed in autoclaved plastic cages covered with filter tops and provided with bedding in a temperature-controlled room (25.5°–27.8° C.) on a 12-hour light:dark cycle. The diets and pH 2.5 acidified distilled water were made available to the animals ad libitum.

35 $mm^3$ of finely minced MX-1 human mammary adenocarcinoma tissue were suspended in a cell culture medium and injected subcutaneously to female BALB/c (nu/nu) mice proximal to the right #4 mammary gland using a 16 gauge needle under sterile conditions.

The transplantable MX-1 human breast carcinoma is derived from a primary breast tumor. Samples of the carcinoma were obtained from the EG&G Mason Research Institute (Worcester, Mass.)

Example 5

Effect of Various Diets on the Transplanted Tumors.

The mice were maintained on a standard laboratory diet (Purina Mouse Chow #5058) which contains 9 wt. % fat of which approximately 50 wt. % are fatty acids (FA) in the form of linoleate.

Figure 3:
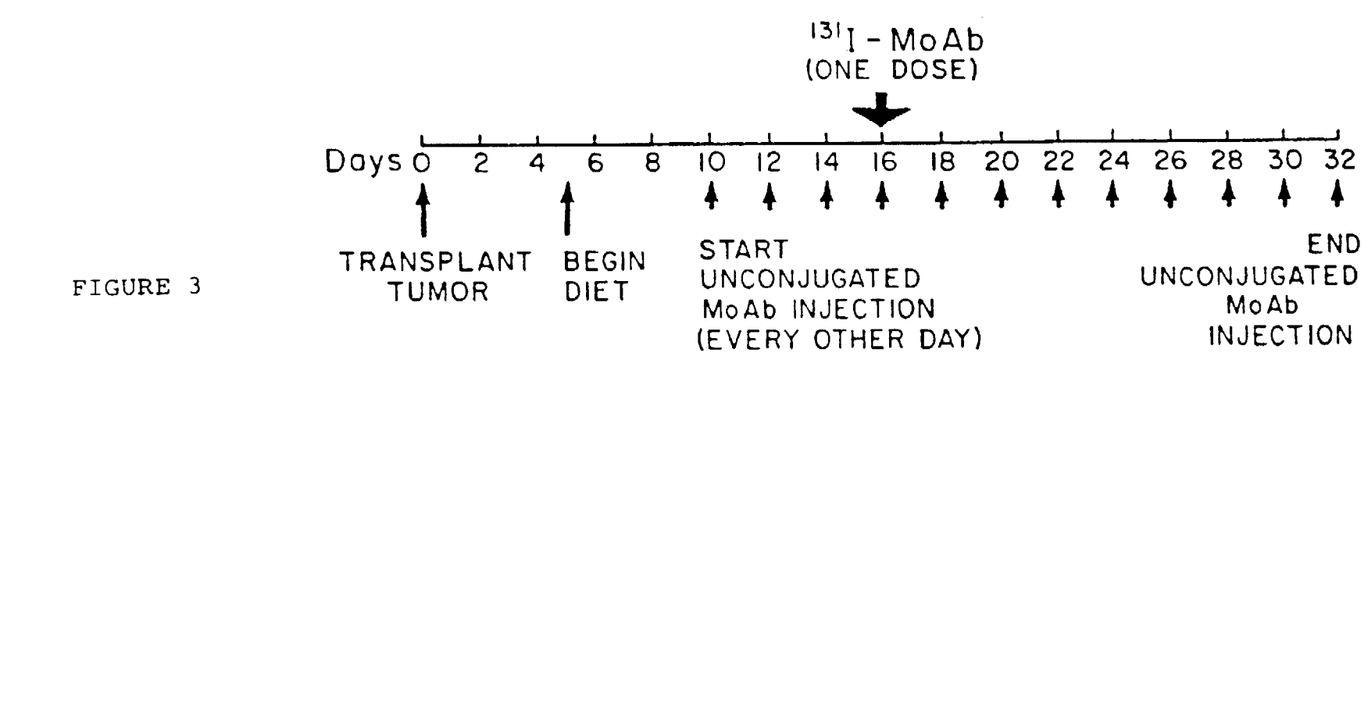
FIG. 3 depicts the experimental design showing the day of initiation of tumor transplantation of the diet consisting of (1) fish oil (MaxEPA), (2) corn oil or (3) lard, and day of injections of "the monoclonal antibody" (MoAb) (Mc1, Mc3, Mc5 and Mc8) cocktail either unconjugated or (b) $^{131}$I-labeled of BALB/c nude mice carrying the human transplantable breast tumor MX-1.

5 days after implantation, 5 mice each were given a designated, semi-purified isocaloric experimental diet containing 11 wt. % fat as shown in FIG. 3. The fat component consisted of either lard, corn oil (CO) or (MaxEPA).

As in the previous examples the basis for all test diets was a fat-free dry mixture which contained by weight the following components.

53.75% sucrose;

24.0% vitamin-free casein;

3.75% salt mixture (AIN #76);

2.2% vitamin mixture (vitamin diet fortification mix, (ICN Nutritional Biochemicals, Cleveland, Ohio);

0.3% methionine;

5.0% cellulose; and 0.01% butylated hydroxytoluene.

The fat-containing diets were made by adding each fat or oil to the dry mixture at 11 wt. %. The fat component included either lard (Armour Food Co., Omaha, Nebr.), CO (Willsey Foods, Inc., City of Industry, Calif.) or MaxEPA (R. P. Sherer Corp., Clearwater, Fla.). The animal diets were made fresh twice a week, dried and then frozen. A new batch of pellets was replaced daily to standardize the intake of the FA and to prevent their possible peroxidation if left in the cages for longer periods of time.

The administration of isocaloric diets containing lard, CO and MaxEPA as the sole fatty acid (FA) source did not diminish the rate of body weight increase of the tumor-bearing mice.

As shown in the previous example, the group receiving the MaxEPA diet showed an even higher average body weight at the end of the experiment than the lard and CO fed groups.

Moreover, these results were determined to be statistically significant. In addition, the PUFA from fish oils were shown to interfere with the growth of breast tumors. These data are supportive of previous results (Begin, M. E. et al., "Polyunsaturated fatty acid-induced cytotoxicity against tumor cells and its relationship to lipid peroxidation", JNCI 80:188–194 (1988)).

The inhibition of tumor growth (% IG) produced by MaxEPA at 32 days was determined to be 64% when compared to the effect of CO, and 59% when compared with the effect of lard. These data are shown in FIG. 2 and Table 1. By contrast, the administration of CO to the animals showed no effect when compared to the lard group. The results are shown in Table 3 below.

TABLE 3

Control and MoAb-treated groups fed the three different diets

| Fat Source | Treatment | Day[a] | Tumor[b] Volume | (% IG)[c] | (% IG)[d] | (% IG)[e] |
|---|---|---|---|---|---|---|
| Lard | None | 32 | 1136 ± 182 | — | 11.6[h] | — |
|  | MoAb | 32 | 1262 ± 663 | −15.0[f] | −5.5[f] | −15.0[f] |
|  | 131I-MoAb | 32 | 272 ± 63 | 76.1[g] | 78.3[g] | 76.1[g] |
| Corn Oil | None | 32 | 1146 ± 283 | — | — | −13.2[h] |
|  | MoAb | 32 | 586 ± 107 | 48.9[f] | 48.9[f] | 42.7[f] |
|  | 131I-MoAb | 32 | 236 ± 72 | 79.4[g] | 79.4[g] | 77.3[g] |
| MAX-EPA | None | 32 | 412 ± 96 | — | 63.8[h] | 59.1[h] |
|  | MoAb | 32 | 605 ± 70 | 51.3[f] | 45.2[f] | 36.8[f] |
|  | 131I-MoAb | 32 | 70 ± 32 | 83.0[g] | 90.7[g] | 89.7[g] |

[a]Tumor transplantation was at day 0, initiation of diet at day 5, unconjugated and 131I-conjugated MoAb therapy initiated at days 10 and 16 respectively (FIG. 1).
[b]in mm³ + standard error (SE).
[c]% IG calculated using the same dietary fat source as (Cn) v. corresponding untreated fat source.
[d]% IG calculated using Corn Oil dietary fat source control as Cn v. Corn Oil untreated.
[e]% IG calculated using Lard dietary fat source control as Cn v. untreated Lard.
[f]To and Co are calculated using day 10 after tumor transplantation on which day unconjugated MoAb therapy was initiated.
[g]To and Co are calculated using day 16 after tumor transplantation on which day 131I-MoAb therapy was initiated.
[h]To and Co are calculated using day 5 after tumor transplantation on which day the different lipid diets were initiated.

Unsaturated FA with high content of eicosapentonoic acid (omega-3 PUFA) show effectiveness in arresting the growth of transplantable MX-1 human breast tumor in nude mice. It should be remarked that the growth of this tumor resembles that of a large number of human breast tumors in that it is hormone-independent (Inoue, K et al., "Antitumor efficacy of seventeen anticancer drugs in human breast cancer xenograft (MX-1) transplanted in nude mice", Cancer Chemother. Pharmacol. 10:182–186 (1983)).

Thus, the action of the omega-3 PUFAs and omega-6 can not be ascribed to interference with hormonal stimuli affecting the breast tumor cells. Together with this ability of the omega-3 PUFA to inhibit breast tumor growth, PUFA also induces the growth of a cell population that is not inhibited further in its growth by unconjugated anti-breast epithelial MoAbs in doses that are clearly growth inhibitory when the tumor hosts are fed an isocaloric diet supplemented with high content of unsaturated FA consisting mainly of linoleic acid (omega-6 PUFA) as shown in this study, or a standard mouse chow (Purina 5058 with 9 wt. % fat in accordance with Begin et al. as shown by Begin et al. (Begin, M. E., et al., "Differential killing of human carcinoma cells supplemented with n-3 and n-6 polyunsaturated fatty acids", JNCI 77:1053–1062 (1986)).

Example 6
Preparation of the Monoclonal Antibodies.

Hybridoma cell lines producing MoAbs Mc1, Mc3, Mc5, and Mc8 (Ceriani, R. L. et al., "Characterization of cell surface antigens of human mammary epithelial cells with monoclonal antibodies prepared against human milk fat globule", Somat. Cell Genet. 9:415–427 (1883); Ceriani, R. L. et al., "Circulating human mammary epithelial antigens (HME-Ags) in breast cancer", Proc. Natl. Acad. Sci. (USA) 79:5421–5424 (1982)) were injected into 2,6,10,14-tetramethylpentadecane primed BALB/c mice.

Ascites were collected under sterile conditions and the cells were removed by centrifugation at 150×g for 5 min.

The ascites' supernatant was then centrifuged at 20,000×g for 10 min at 4° C. and then frozen at -80° C. until used as needed.

The ascites' supernatant was thawed prior to use, centrifuged at 40,000×g for 15 min., diluted 1:1 with 0.05M phosphate buffer and filtered through a 0.2µ cellulose acetate filter (Nalgene, Sybron, Rochester, N.Y.). Thereafter, immuno-globulins (Ig) were separated by means of a hydroxyapatite preparatory column (2.5 cm×5.0 cm, Bio-Rad, Richmond, Calif.) with a sodium phosphate gradient (0.01 to 0.3M) containing 0.01 nM $CaCl_2$. The purified fractions of Igs were concentrated with a CS-30 Immersible Membrane (Millipore, Bedford, Mass.), and made sterile by filtration in a 0.2 u cellulose acetate filter (Millipore, Bedford, Mass.).

Pyrogen testing was conducted to determine the presence of endotoxin after final MoAb purification using the Limulus Amoebocyte Lysate test (Mallinckrodt, St. Louis, Mo.). The samples were considered pyrogen free if the amount of endotoxin was below the level which is detectable by the test (0.06 ng/ml). All solutions were prepared in pyrogen free water (Abbott Laboratories, N. Chicago, Ill.).

Example 7
Effect of Various Diets and Unconjugated Monoclonal Antibodies on the Tumors.

Five days after being placed on the experimental diets and therefore 10 days after tumor grafting, the mean tumor volume was about 40 mm. At this time five mice from each group were injected i.p. samples containing 2.4 mg total protein. Each injection contained about 2.4 mg total protein composed of 0.6 mg each of Mc1, Mc3, Mc5 and Mc8 mouse MoAbs to human milk fat globule antigens as shown in FIG. 3.

A total of 10 i.p. injections of MoAb were given each animal at 48 hour intervals. The Mc1 and Mc5 MoAbs recognize 400,000 dalton components and the other two, Mc3 and Mc8 recognize 45,000 dalton components of human milk fat globule membrane (Ceriani, R. L. et al., "Circulating human mammary epithelial antigens (HME-Ags) in breast cancer", Proc. Natl. Acad. Sci. (USA) 79:5421–5424 (1982); Ceriani, et al., Somat. Cell Gen. 9:415 (1983); Salinas, et al., Cancer Res. 47:907 (1987)).

Changes in animal weight and in tumor volume were determined before each MoAb injection and up to 32 days post implantation of the Mx-1. Tumor volumes were calculated from caliper measurements of 3 perpendicular dimensions by means of the following equation.

$$volume\ (mm^3) = (length \times width \times depth)/2.$$

The animals were weighed, bled and sacrificed 20 days after the first injection of MoAbs and the tumors were excised, trimmed, and weighed.

The calculation of the inhibition of growth (% IG) was performed using the following formula.

$$\%IG = (1 - Tn/To/Cn/Co) \times 100,$$

wherein

To and Tn are the average tumor volumes at day 0 or the day of initial unconjugated or radioconjugated MoAb injections and day n for the treated groups respectively, and Co and Cn are the average tumor volumes at day 0 or day of initiation of diet and day n for the control groups respectively.

(Inoue, K. et al., "Antitumor efficacy of seventeen anticancer drugs in human breast cancer xenograft (MX-1) transplanted in nude mice", Cancer Chemother. Pharmacol. 10:182–186 (1983)).

Negative values can be obtained by this calculation. Such values signify a lack of IG or a larger tumor volume of the experimental when compared to the control.

Example 8
$^{131}$I-conjugation of Monoclonal Antibodies.

Iodination of antibodies was carried out with $^{131}$I (8–12 Ci/mg, NEN Research Products, Boston, Mass.). The MoAb mixture was iodinated using 0.5 mg/ml chloramine-T as described in Ceriani et al (1988) and Greenwood et al. (1963) utilizing MoAb concentrations of 4–10 mg/ml. (Ceriani, et al. J. Cancer Res. 48:4664 (1988); Greenwood, et al., Biochem. 89:114 (1963)).

Two milligrams of a mixture of Mc1, Mc3, Mc5, and Mc8 MoAbs having equal protein amounts were labeled. The final conjugate was made to contain up to one molecule of $^{131}$I per molecule of Ig. The samples were counted in a gamma counter (Multi-Prias 4, Packard Corporation, Downers Grove, Ill.).

Example 9
Administration of the Radiolabelled Monoclonal Antibodies.

For radioimmunotherapy experiments, intraperitoneal (i.p.) injections of 500 µCi labeled monoclonal antibodies (MoAbs) were administered on day 16 to a group of nude mice carrying tumors. The animals were then placed in separate cages, fed and provided acidified water as described above. The sequence of procedures for this experiment are shown in FIG. 3.

2 mg of potassium iodide in phosphate buffered saline (PBS) were injected i.p. 1 hr. before every injection of radioiodinated MoAb to block thyroid radioiodine uptake.

The standard error of the mean value (SE) and the statistical significance of the results obtained were calculated as previously reported using the Student t test (Snedecor, et al., Statistical Methods, Iowa State U., Ames, I.A. (1967)).

Example 10
Results of Concomitant Treatment with Various Diets and Conjugated or Unconjugated Monoclonal Antibodies.

Figure 4:
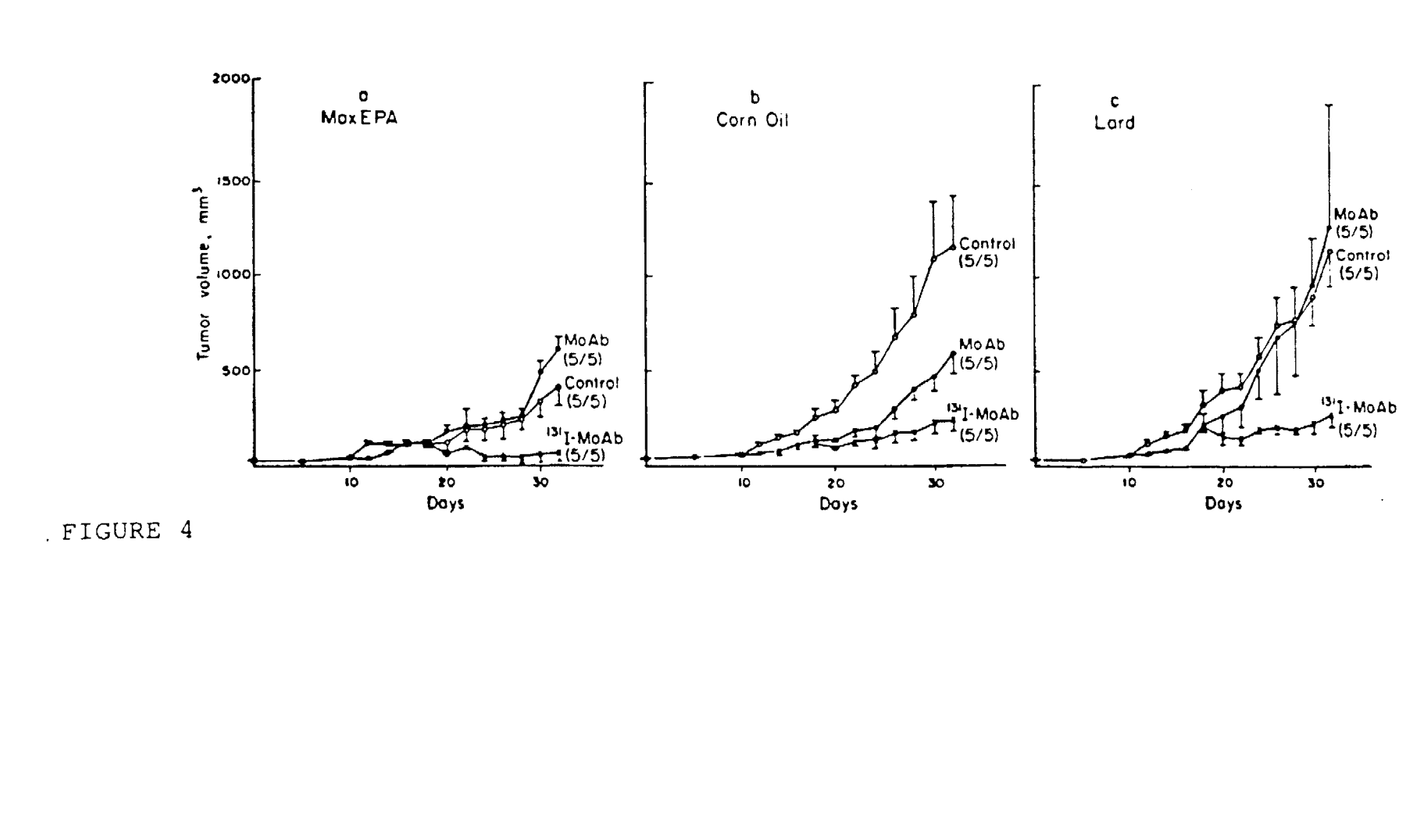
FIG. 4A shows the effects of dietary fat consisting of MaxEPA and immunological therapy with a MoAb (Mc1, Mc3, Mc5, and Mc8) cocktail unconjugated or $^{131}$I-labeled of established transplantable human breast tumor MX-1 in nude mice.
FIG. 4B shows the effect of dietary fat consisting of corn oil and immunological therapy with a monoclonal antibody (Mc1, Mc3, Mc5, and Mc8) cocktail unconjugated or $^{131}$I-labeled of established transplantable human breast tumor MX-1 in nude mice. The bars indicate the standard error of the mean value obtained for 5 animals.
FIG. 4C shows the effect of dietary fat consisting of lard and immunological therapy with a monoclonal antibody (Mc1, Mc3, Mc5, and Mc8) cocktail unconjugated or $^{131}$I-labeled of established transplantable human breast tumor MX-1 in nude mice. The bars indicate the standard error of the mean value obtained for 5 animals.

Anti-human milk fat globule MoAbs were administered either $^{131}$I-conjugated or unconjugated to the three groups of the tumor-bearing mice fed the three diets. $^{131}$I-conjugated MoAbs were administered as in Ceriani et al. (1988) (Ceriani, et al., Cancer Res. 48:466-i (1988)). These data are shown in FIG. 4.

A clear cut effect of the unconjugated MoAbs was shown in terms of % IG at 32 days when comparing the CO group with its control and with the lard group (49% and 43% respectively). These results are shown in FIGS. 4ab and 4c. However, the % IG was near zero for the lard and MaxEPA groups (-15 vs -51%), when compared to their, own untreated controls FIGS. 4c and 4a).

Any % IG obtained in the MaxEPA group when the animals were injected the unconjugated MoAbs and compared to the CO and lard untreated controls can thus be attributed to an overall slower growth induced by MaxEPA on breast tumors. These data are shown in Table 3 above.

To test the modifications introduced by the diet to the already established tumoricidal effect of $^{131}$I-conjugated anti-breast epithelial MoAbs as shown in Ceriani, et al. (Ceriani et al. Cancer Res. 48:4664 (1988)), 1500 µCi $^{131}$I-labeled mixture of the above-described MoAbs were injected to nude mice grafted with the MX-1 tumor and fed the CO, lard, and MaxEPA diets described above. The data obtained are shown in FIG. 4. No loss of body weight or any exterior signs of toxicity were noted in any group.

A simple way of measuring the destruction of a tumor cell population or cytotoxicity is by measuring the shrinkage in volume of subcutaneously grafted tumors following $^{131}$I-conjugated MoAb injection. Thus, the administration of 1500 µCi $^{131}$I-conjugated MoAb was observed to diminish tumor volume to 47.3 mm$^3$ (or to 42.3% of the pre-injection tumor volume) at day 12 after injection in the MaxEPA group. These data are shown in FIG. 4a. In fact, the volume of the original tumor was not regained until day 26 after injection or 42 days after transplantation (data now shown).

In contrast, reduction of tumor volume was only transient in the CO group. The maximum reduction observed was 78.9% of the pre-treatment volume and it lasted only 6 days before the tumor regained its original volume. This can be seen in FIG. 4c.

In the lard-fed group (FIG. 4c) the injection of the $^{131}$I-cocktail conjugate could not bring the tumor volume down to its original volume at the time of $^{131}$I-MoAb injection (FIG. 4c).

Steady tumor growth was then regained 12–14 days after $^{131}$I-conjugate injection in the lard and CO groups whereas such rate of tumor growth was not regained by the MaxEPA group treated with $^{131}$I-MoAbs until day 30 after injection.

The assessment of the effectiveness of $^{131}$I-MoAb treatment was performed by measuring the tumor volumes of control untreated animals under a given diet vs. animals treated with $^{131}$I-conjugated MoAbs and then calculating the % IG.

At day 32 after transplantation of the MX-1 tumor and 16 days after injection of $^{131}$I-MoAbs the mean tumor volume of the lard fed group was 272+63 mm$^3$, that of the CO-fed group was 236+72m$^3$, and that of the MaxEPA-fed group was only 70+32 mm$^3$. These data are shown in FIG. 4. The MaxEPA-fed group tumor volumes were statistically different from those of the CO-fed group (p 0.05) and of the lard-fed group (p 0.025) as can be seen from Table 3 above.

The % IG for $^1$I-MoAb treated lard, CO and MaxEPA groups at day 32 after initiation of the experiment were 76, 79 and 83%, respectively, when compared to its corresponding untreated controls. This is shown in Table 3 above.

Since the body weights of the MX-1 tumor-bearing BALB/c nude mice differed somewhat from group to group, changes in body weight were calculated and then statistically analyzed. The MaxEPA control and MaxEPA unconjugated MoAb injected groups showed statistically significant weight increases over the period from days 5 to 32, p 0.05 for each group. On the other hand, the CO and lard controls and unconjugated MoAb injected groups showed no statistically significant increases.

In addition, no statistically significant changes in body weight occurred in the $^{131}$I-MoAb injected group for all three diets. However, there was a statistically significant increase from days 16 to 32 for the Max-EPA control group vs $^{131}$I-MoAb injected group since the MaxEPA control group showed an increase in body weight whereas the $^{131}$I-MoAb injected group showed a slight decrease in body weight.

Lard and CO diet fed groups showed no statistically significant weight differences between control and $^{131}$I-MoAb injected groups.

Lastly, the MaxEPA control group showed the largest increase in body weight over the period from day 5 to 32 which was statistically significant only in the case of the MaxEPA-fed group vs. lard (p 0.05).

Nude mice grafted with the transplantable human breast tumor MX-1 fed a Purina 5058 diet which is essentially similar to the isocaloric CO-supplemented diet of this study had been shown to respond with a continued large % IG of their tumors when $^{131}$I-conjugated anti-human milk fat globule MoAbs were injected (Ceriani, et al., Cancer Res. 48:4664 (1988)).

The tumors existing in the MaxEPA-fed animals after $^{131}$I-MoAb treatment were reduced in volume below pre-$^{131}$I-MoAb treatment values and remained below the initial tumor volume for as many as 26 days after injection. However, tumors in CO-fed animals had volumes below pretreatment values for only 4 days and tumors in lard-fed animals had no reductive response. This acute reduction in tumor volume after $^{131}$I-conjugated MoAb injection represents the actual tumor destruction instituted by the therapy.

The higher efficiency of $^{131}$I-conjugates for the treatment of breast tumors in MaxEPA-fed animals is also demonstrated when a comparison is made of the % IG at day 16 of $^{131}$I-MoAb treatment (% IGs 90.7 and 89.7, respectively) with groups fed CO (% IGs 79.4 and 77.3 respectively) and lard (% IGs 78.3 and 76.10 respectively), using the untreated CO- or lard-fed group as controls. These data are provided in Table 3 above.

This advantage is thus proved (1) absolutely: by comparing the final tumor volumes among the three diet groups treated with $^{131}$I-MoAbs; and (2) relatively: by comparing $^{131}$I-MoAb treated MaxEPA-fed group vs. untreated lard or CO-fed groups.

The data are shown in Table 3 above.

Of considerable interest is that the lard-fed group of animals did not respond to unconjugated MoAb treatment but did respond to $^{131}$I-MoAb conjugate treatment as can be seen from FIG. 4c and Table 3 above.

On the contrary, the CO-fed group responded to 9 both $^{131}$I-conjugated and unconjugated MoAbs, although they responded better to the latter as can be seen in FIG. 4b. The reasons for these results are unclear. However, the action of $^{131}$I-conjugated MoAbs in the CO group can be attributed to the presence of a high level of linoleate 59.7 wt % (18:2, omega-6). This fatty acid has been involved in the intermediary levels of cytotoxicity on breast tumor cells via a lipid peroxidation mechanism and formation of free radicals (Begin, M. E., et al., "Polyunsaturated fatty acid-induced cytotoxicity against tumor cells and its relationship to lipid peroxidation", J. Nat. Cancer Inst., 80:188 (1988)).

By following this hypothesis the higher effectiveness of MaxEPA can be attributed to its higher level of eicosapentonoic acid (20:5, omega-3) which might therefore contribute to its even higher peroxidation ability (Beguin, M. E. et al. (1988), supra).

The effectiveness of $^{131}$I-MoAb therapy as measured by tumor volume reduction was maintained for a much longer period and to a much higher % IG in the MaxEPA-fed group than in the CO-fed group here, and in animals fed Purina 5058 having 9 wt % mixed animal and vegetable fat (Ceriani, et al., Cancer Res. 48:4664 (1988)). Thus, a dietary fat source from fish oils has been shown to increase the efficiency of the $^{131}$I-conjugated MoAb attack on the human breast tumor MX-1.

The continued inhibition of breast tumor growth induced by omega-3 and omega-6 PUFAs, (e.g., 20:5 and 22:6) in fish oils also reduces the ability of the $^{131}$I-conjugated MoAb treated tumors to regain growth. Thus, under a diet of high omega-3 PUFAs, the magnitude and duration of the response to $^{131}$I-MoAbs is heightened and lengthened, thus permitting the eradication of tumors in patients by the administration of appropriately spaced therapeutic doses.

These results support the view that a diet containing MaxEPA as a fat source enhances the activity of a $^{131}$I-conjugated anti-human milk fat globule MoAbs on breast tumors substantially in the absence of toxic side effects.

Example 11

Histopathological Studies

Normal and neoplastic human tissues were either frozen/sectioned, or fixed with either 10% formaldehyde or absolute ethanol, embedded in paraffin blocks, and sectioned at 5 microns thickness. These tissues were utilized for histopathological studies. The tissues were obtained from different organs in accordance with the above procedure, antibody added and the tissues were then stained for antibody binding by immunoperoxidase procedures. (Battifora, H., Sem. Diag. Pathol. 1:251 (1984)). The data obtained are shown below in Table 4 (normal tissues), Table 5 (pathological tissues) for MoAb Mc5, Table 6 (normal and pathological tissues) for MoAb Mc8, Table 7 (normal and pathological tissues) for MoAb Mc1 and Table 8 (normal and pathological tissues) for MoAb Mc3.

TABLE 4

Histological Normal Tissue Distribution of MoAb Mc5

| | |
|---|---|
| Breast | + |
| Lung | + |
| Kidney | + |
| Esophagus | + |
| Pancreas | + |
| Salivary Gland | + |
| Thyroid | + |
| Sebaceous and Apocrine glands | + |
| Stomach | − |
| Brain | − |
| Bladder | − |
| Muscle | − |
| Myocardium | − |
| Skin (Epider.) | − |
| Small Intestine | − |
| Spleen | − |
| Lymph Node | − |
| Adrenal | − |
| Liver | − |

TABLE 5

Histopathological Neoplastic Tissue Distribution of MoAb Mc5

| | |
|---|---|
| Breast CA (form.) | 155/163 |
| Breast CA (EtOH) | 48/48 |
| Breast CA (frozen) | 40/40 |
| Cervical CA | 2/3 |
| Cholangia CA | 1/1 |
| Colon CA | 5/14 |
| Ret. Embryonal CA | 1/1 |
| Endometrial CA | 12/13 |
| Hepatoma | 1/5 |
| Lung CA | 15/15 |
| Ovarian CA | 15/17 |
| Pancreatic CA | 11/14 |
| Prostatic CA | 1/15 |
| Renal Cell CA | 5/15 |
| Salivary CA | 1/2 |
| Salivary Adenoma | 0/5 |
| Warthins Tumor | 2/2 |
| Salivary Mixed Tumor | 1/1 |
| Stomach CA | 4/6 |
| Thyroid | 6/6 |
| Undiff. CA | 10/29 |
| Mesothelioma | 5/10 |

TABLE 6

Histopathological Tissues Distribution of MoAb Mc8

| Normal Tissue | all negative |
|---|---|
| Carcinomas: | |
| (a) weak staining on breast tumors (24/49[1], 14/55[2], 6/40[3]); | |
| (b) negative on all other carcinomias of: | |
| cervix, | |
| colon, | |
| duodenum, | |
| endometrium, | |
| kidney, | |
| liver, | |
| lung, | |
| ovary, | |
| pancreas, | |
| parathyroid, | |
| prostate, | |
| stomach, and | |
| thyroid. | |

[1]Ethanol Fixed
[2]Formalin Fixed
[3]Frozen Sectioned

TABLE 7

Histopathological Tissue Distribution of MoAb Mc1

Normal tissues:

stains distal tubules of:
kidney,
alveoli of lung, acini of pancreas,
salivary gland,
sebaceous glands,
apocrine glands, and
esophagus endometrium.
Carcinomas:

breast (45/29[1], 52/54[2], 38/40[3]),
cervix (3/3[1], 3/5[2]),
colon (0/6[1], 1/5[2]),
duodenum (0/1[1], 1/2[2]);
endomedetrium (3/3[1], 4/5[2]),
kidney (2/8[1], 6/6[2]),
meningioma (0/1[2]),
ovary (8/8[1], 6/8[2]),
pancreas (2/2[1], 2/2[2]),
prostate (0/2[2], 1/3[2]),
salivary gland (6/9[2], 1/1[2]),
stomach (5/12[2]),
thyroid, (0/2[1], 2/3[2]), and
mesothelioma (3/10[2]).

[1]Ethanol Fixed
[2]Formalin Fixed
[3]Frozen Sectioned

TABLE 8

Histopathological Tissue Distribution of MoAb Mc3

Normal tissues:

all negative[1,2].
Carcinomas:

Weak staining on
breast tumors (24/29[1], 14/55[2], 6/40[3]),
negative on all other carcinomas tested including
cervix,
colon,
duodenum,
endometrium,

TABLE 8-continued

Histopathological Tissue Distribution of MoAb Mc3 kidney,
liver,
lung,
ovary,
pancreas,
parathyroid,
prostate,
stomach, and
thyroid.

[1]Ethanol Fixed
[2]Formalin Fixed
[3]Frozen Sectioned

The invention now being fully described, it will be apparent to one of ordinary skill in the art that many changes and modifications can be made without departing from the spirit or scope of the invention as set forth herein.

We claim:

1. An in vivo tumorcidal method for malignant human breast tumor cells, comprising administering to a subject in need of such treatment at least one radiolabeled antibody binding a human milk fat globule (HMFG) differentiation antigen, the antigen cross-reacting with the malignant tumor cells; and administering to the subject at least one product comprising an agent selected from the group consisting of polyunsaturated fatty acids, pharmaceutical salts thereof and mixtures thereof, the antibody and the product being administered in amounts which jointly produce an effective tumorcidal effect.

2. The method of claim 1, wherein one antibody is labeled with a radioactive atom selected from the group consisting of $^{131}$I, $^{90}$Y, $^{212}$Bi, $^{221}$At, $^{99}$mTc, $^{186}$Re, and mixtures thereof.

3. The method of claim 1, wherein the polyunsaturated fatty acids are selected from the group consisting of fish oil-type fatty acids, cyclooxigenase products, 5-, 12- and 15-cyclooxygenase products, monooxigenase products, $C_{17}$-hydroxy fatty acids, 12-HpETE and 12-HETE, analogues thereof, pharmaceutically-acceptable salts thereof and mixture thereof.

4. The method of claim 1, wherein the polyunsaturated fatty acids are selected from the group consisting of derived essential fatty acids, omega-3 and omega-6 polyunsaturated fatty acids and combinations thereof, analogues thereof, pharmaceutically-acceptable salts thereof and mixtures thereof.

5. The method of claim 1, wherein one of the polyunsaturated fatty acids are ($C_6$–$C_{30}$) fatty acids comprising three or more unsaturated bonds, analogues thereof, pharmaceutically effective salts thereof, and mixtures thereof.

6. The method of claim 1, wherein one antibody is a monoclonal antibody.

7. The method of claim 1, wherein the amount of polyunsaturated fatty acids is about 0.3 to 6.0 g per kg of body weight of the subject and it is administered every about 1 to 60 hrs.

8. The method of claim 1, further comprising administering to the patient an antitumor therapy selected from the group consisting of surgery, chemotherapy, hormonal therapy, external and internal radiotherapy, hyperthermic therapy, biological response modifiers and combinations thereof.

9. The method of claim 1, wherein when the polyunsaturated fatty acids are administered orally they are added to the subject's food in an amount of about 1 to 50 wt % thereof.

10. A radioimmunotherapy tumorcidal kit, comprising in separate containers an antitumor agent selected from the group consisting of antibodies binding a human milk fat globule (HMFG) antigen, which cross-react with malignant tumor cells, and mixtures thereof;

wherein at least one of the antibodies radiolabeled;

a composition comprising at least one agent selected from the group consisting of polyunsaturated fatty acids, pharmaceutically acceptable salts thereof, and mixtures thereof; and instructions for binding a radiolabel to at least one antibody prior to administration and/or instructions for administration of the radiolabeled antitumor agent.

11. The kit of claim 10, further comprising at least one syringe and needle for self administration.

12. The kit of claim 10, wherein one antibody is a monoclonal antibody.

13. The method of claim 1, further comprising prior to the administration of the radiolabeled antibody obtaining at least one antibody binding the human milk fat globule (HMFG) differentiation antigen, wherein the antigen cross-reacts with malignant tumor cells; and binding a radiolabel to the at least one antibody.

14. The kit of claim 10, wherein at least one antibody is to be labeled with a radioactive atom selected from the group consisting of $^{131}$I, $^{9}$OY, $^{212}$Bi, $^{221}$At, $^{99m}$Tc, $^{186}$Re, and mixtures thereof.

15. The kit of claim 10, wherein the composition is in the form of a pharmaceutically acceptable composition.

16. The kit of claim 10, wherein the antitumor agent is administered in the form of a pharmaceutically acceptable composition.

17. The kit of claim 10, wherein the fatty acids are selected from the group consisting of ($C_6$–$C_{50}$) fatty acids comprising three or more double bonds, pharmaceutically-acceptable salts thereof and mixtures thereof.

18. The kit of claim 10, wherein the antitumor agent is provided in a closed sterile container; and the composition is provided in the form of a powder, capsules, dragees, tablets, a liquid solution or suspension or suppository.

19. The method of claim 1, wherein the product is in the form of a pharmaceutically acceptable product.

20. The method of claim 1, wherein the antibody is administered in the form of a pharmaceutically acceptable composition.

* * * * *

UNITED STATES PATENT AND TRADEMARK OFFICE
CERTIFICATE OF CORRECTION

PATENT NO. : 5,766,571
DATED : June 16, 1998
INVENTOR(S) : Roberto L. Ceriani and Jerry A. Peterson It is certified that error appears in the above-identified patent and that said Letters Patent is hereby corrected as shown below:

Title page,
Item [56], References Cited, OTHER PUBLICATIONS, change "Antiybody" into -- Antibody --.
Change "enzuyme" into -- enzyme --.
Change "Lacet" into -- Lancet --.
Change "Blobule" into -- Globule --.
Change "Chamical" into -- Chemical --.
Change "Breats" into -- Breast --.

Column 2,
Lines 63-64, change ", internal irradiation" into -- agents --.

Column 8,
Line 19, change "ax" into -- a --.

Column 10,
Line 48, change "ire" into -- are --.

Column 11,
Line 47, change "purchases" into -- purchased --.
Line 52, change "an" into -- ad --.

Column 18,
Line 15, change "4c" into -- 4b --.
Line 37, change "$^1$I-MoAb" into -- $^{131}$I-MoAb --.

Column 19,
Line 32, delete "9".

Column 21,
Line 9, change "carcinonias" into -- carcinomas --.

Column 22,
Line 35, change "$^9$OY, $^{21}$2Bi, $^{22}$1AT, $^{99}$mTc, $^{18}$6Re" into -- $^{90}$Y, $^{212}$Bi, $^{221}$At, $^{99}$mTc, $^{186}$Re --.

UNITED STATES PATENT AND TRADEMARK OFFICE
CERTIFICATE OF CORRECTION

PATENT NO. : 5,766,571
DATED : June 16, 1998
INVENTOR(S) : Roberto L. Ceriani and Jerry A. Peterson It is certified that error appears in the above-identified patent and that said Letters Patent is hereby corrected as shown below:

Column 23,
Line 7, after "antibodies" insert -- is --.

Column 24,
Line 3, change "$^9OY, ^{21}2Bi, ^{22}1At$" into -- $^{90}Y, ^{212}Bi, ^{221}At$ --.

Signed and Sealed this

Fifteenth Day of October, 2002

Attest:

JAMES E. ROGAN
Attesting Officer              Director of the United States Patent and Trademark Office